(12) United States Patent
Gabelman et al.

(10) Patent No.: US 6,353,156 B1
(45) Date of Patent: Mar. 5, 2002

(54) HIGH PIGMENT BEET

(75) Inventors: Warren H. Gabelman; Irwin L. Goldman, both of Madison; D. Nicholas Breitbach, Middleton, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/501,178

(22) Filed: Feb. 10, 2000

(51) Int. Cl.$^7$ .................................................. A01H 5/00
(52) U.S. Cl. ........................................ 800/298; 800/260
(58) Field of Search .................................. 800/260, 298

(56) References Cited

PUBLICATIONS

Eagen, K.A., et al., (Abstract of) "RAPD Marker Frequency Changes in Two Red Beet Populations Undergoing Recurrent Selection" (1994), HortScience 29(5):478.

Eagen, K.A., et al., (Abstract of) "Directional RAPD Marker Frequency Changes in Two Divergently Selected Beet Populations" (1995), HortScience 30(4):841.

Eagen, K.A., et al., "RAPD Marker Frequency Changes Associated with Sugar and Pigment Content in Two Beet Populations Modified Via Recurrent Selection," Proceedings of the 28th Biennial Meeting of the Am. Soc. of Sugar Beet Technologists, New Orleans, LA, Mar. 8–11, 1995, pp. 99–105.

Eagen, K.A., (Abstract of) "RAPD Marker Frequency Changes in Two Beet Populations Resulting from a Divergent Recurrent Selection Scheme," Proceedings of 1995 International Conference on the Status of Plant Genome Research III, San Diego, CA, p. 40.

Eagen, K.A., et al. (1996), "Assessment of RAPD marker frequencies over cycles of recurrent selection for pigment concentration and percent solids in red beet (Beta vulgaris L.)," Mol. Breeding 2:107–115.

Goldman, I.L. (1996), "A List of Germplasm Releases from the University of Wisconsin Table Beet Breeding Program, 1964–1992," HortScience 31(5):880–881.

Goldman, I.L., et al. (1995), (Abstract of) "Response to Eight Cycles of Half Sib Family Recurrent Selection for Pigment Concentration in Beta vulgaris," Agronomy Abstracts, p. 97.

Goldman, I.L., et al. (1996), "Simultaneous Selection is Effective in Increasing Betalain Pigment Concentration but not Total Dissolved Solids in Red Beet," J. Amer. Soc. Hort. Sci. 121(1):23–26.

Goldman, I.L., et al., "Genetic Modification of Betalain Pigment Concentration in Red Beet (Beta vulgaris L.)" Proceedings of the 1996 International Conference on Natural Colorants, Acapulco, Mexico, Jan. 23–25, pp. 1–3.

Watson, James F., et al. (1982), "Seasonal Changes and Cultivar Differences in pigment Concentrations and Percent Dissolved Solids in Roots of Table Beets," J. Amer. Soc. Hort. Sci. 107(5):713–716.

Watson, James F., et al. (1984), "Genetic Analysis of Betacyanin, Betaxanthine, and Sucrose Concentrations in Roots of Table Beet," J. Amer. Soc. Hort. Sci. 109(3):386–391.

Wolyn, D.J., et al. (1986), "Effects of Planting and Harvest Date on Betalain Pigment Concentrations in Three Table Beet Genotypes," HortScience 21(6):1339–1340.

Wolyn, D.J., et al.(1989), "Inheritance of Root and Petiole Pigmentation in Red Table Beet," J. Heredity 80(1):33–38.

Wolyn, D.J., et al. (1990), "Selection for Betalain Pigment Concentrations and Total Dissolved Solids in Red Table Beets," J. Amer. Soc. Hort. Sci. 115(1):165–169.

*Primary Examiner*—Bruce R. Campell
*Assistant Examiner*—Susan B. McCormick
(74) *Attorney, Agent, or Firm*—Rothwell, Figg, Ernst & Manbeck

(57) ABSTRACT

Novel high pigment beet populations and varieties and methods to produce are disclosed. The invention relates to a beet seed, a beet plant, a beet population, a beet variety, a beet hybrid and to a method of producing beets having a high level of total betalain pigments in the root.

28 Claims, No Drawings

HIGH PIGMENT BEET

BACKGROUND AND SUMMARY OF THE INVENTION

The present invention relates to a beet seed, a beet plant, a beet population, a beet variety, a beet hybrid and to a method of producing beets having a high level of total betalain pigments in the root.

Using color enhancements in food makes certain types of food more aesthetically appealing and appetizing. Previously, research on color enhancement primarily focused on the cosmetic value of colorants until organizations such as the FDA started denying the use of certain colorants. More specifically in the 1970's, the FDA denied the use of certain coal tar dyes for food coloring. In order to avoid the bans placed on synthetic and manufactured colorants, the food industry started looking to natural plant pigments as a food colorant source. For example, beet pigments (betalains) are a native red colorant that is useful as a food coloring. Betalain pigments include the red-violet betacyanins (BC) and the yellow betaxanthins (BX), which when combined, produce a red hue useful in certain foods as a colorant. One source of betalains that is readily available is the garden beet. Thus garden beets have become a source of betalains for the red pigment. The beet juice concentrates and powders made from standard table beets typically contain pigment concentrations of 1% or less. These concentrations are relatively low and therefore require large quantities of beets to reach desired levels of pigment. These low concentrations make the preparation of purified red food colorants from beet sources more difficult and costly than they would be at higher concentrations. Moreover, beet extracts naturally contain solutes, such as sugars, which also hinder the production of high concentrations.

Several breeding experiments have already been done to elevate the betalain concentrations in beets (*Beta vulgaris* L.). The beets were obtained through a recurrent selection process where the highest pigment beets for flowering, open pollination, and subsequent seed production were selected. The beets selected were selected for both increased pigment levels and high and low total dissolved solids. The naturally contained dissolved solids such as sugars in beet extracts have been found to limit the production of highly concentrated pigment solutions for food dyes (von Elbe; J., 1978, The betalains, p. 29–39. In: T. E. Furia (ed.) Current aspects of food colorants. CRC Press, Cleveland, Ohio). Successful selection for concentrations of pigment and dissolved solids depends on the availability of adequate genetic variability for both traits and a favorable genetic correlation between traits a (Wolyn D J and Gabelman W H, 1990, Selection for betalain pigment concentration and total dissolved solids in red table beets. J Amer Soc Hort Sci 115 (1):165–169). The average pigment level in a beet ranges from 75 to 80 milligrams (mg) of pigment per 100 grams (g) fresh weight of the beet. There is a need for a quantitative increase in betalain concentrations to improve the commercial applications of betalain as a food colorant. Beets having high concentrations of pigment would make the preparation of natural red colorants easier and less costly.

SUMMARY OF THE INVENTION

The present invention relates to a beet seed, a beet plant, a beet population and to a method for producing a beet plant.

More specifically, the invention relates to a beet root having high concentrations of betalain pigment of over 310 mg per 100 g of fresh weight.

An aspect of this invention is to provide a beet that has a pigment concentration of greater than 310 mg per g of fresh weight of the beet root which makes the preparation of food colorant from the beet easier and less costly.

Another aspect of this invention is to provide a hybrid beet plant. The present invention further relates to a method of producing a high pigment beet by crossing the high pigment beet of the instant invention with another beet plant.

Another aspect of the present invention to provide populations of red beets having betalain concentrations at levels convenient for commercial purification of pigment for use as food colorants.

It is another aspect of the invention to provide high pigment/low solids and high pigment/high solids beet populations to further facilitate in the production of purified pigment for use as food colorant.

The present invention also relates to the transfer of the increased pigment level into other genetic backgrounds.

The present invention also relates to a method of making a high pigment beet by crossing high pigment/high solids (HPHS) populations with high pigment/low solids (HPLS) populations to produce a beet root having a pigment content of at least 310 mg per 100 g fresh weight of the beet root.

DETAILED DESCRIPTION OF THE INVENTION

In order to provide an understanding of some of the terms in the specification and claims, the following definitions are provided:

Pigment concentration: As used herein, the term "pigment concentration" is the amount of total betalain pigment, including both betacyanin and betaxanthin, in the beet root, expressed as milligrams of pigment per 100 gram fresh weight.

HPHS population: As used herein, the term "HPHS population" is a population of table beet plants undergoing recurrent selection for elevated betalain pigment concentration. The HPHS population was selected for high pigment and high total dissolved solids. The HPHS population was originally formulated by Watson and Gabelman at the University of Wisconsin. Recurrent selection in the HPHS population was continued by Wolyn, Goldman, and Breitbach.

HPLS population: As used herein, the term "HPLS population" is a population of table beet plants undergoing recurrent selection for elevated betalain pigment concentration. The HPLS population was selected for high pigment and low total dissolved solids. The HPLS population was originally formulated by Watson and Gabelman at the University of Wisconsin. Recurrent selection in the HPLS population was continued by Wolyn, Goldman, and Breitbach.

Betalain pigment: As used herein, the term "betalain pigment" is a class of pigments unique to the plant order Caryophylalleles. Betalain pigments are derivatives of betalamic acid and can be classified into two groups: The red-violet betacyanins (BC) and the yellow betaxanthins (BX). These differ by conjugation of a substituted aromatic nucleus to the 1,7-diazaheptamethinium chromophore, which is present in betacyanin.

Betacyanins (BC): As used herein, the term "betacyanins (BC)" is a derivative of betalamic acid that has a conjugated substituted aromatic nucleus to the 1,7-diazaheptamethinium chromophore. Betacyanin is red-violet in color.

Betaxanthins (BX): As used herein, the term "betaxanthins (BX)" is a derivative of betalamic acid that does not contain the conjugated substituted aromatic nucleus to the 1,7-diazaheptamethinium chromophore. Betaxanthin is yellow in color.

Current commercial beets and unselected beet populations typically have betalain concentrations in the range of 70 to 80 milligrams per 100 grams weight of fresh weight beet extract. By using the selection procedures disclosed below in connection with the beet populations, it has been found that it is possible to increase the betalain concentrations in red beet to unexpected levels exceeding 310 mg per 100 g of fresh weight.

In the present invention, a beet having a pigment content of at least 310 mg per 100 g fresh weight of the beet was developed. The pigment content of the present invention may exceed 310 mg per 100 g of fresh weight of the beet. In one embodiment, the pigment content is between 310 mg and 330 mg per 100 g fresh weight of the beet. In another embodiment the pigment content is between 330 mg and 350 mg per 100 g fresh weight of the beet root. The pigment content is between 350 mg and 370 mg per 100 g fresh weight of the beet in another embodiment. In yet another embodiment, the pigment content is between 370 mg and 390 mg per 100 g fresh weight of the beet. In still another embodiment, the pigment content is between 390 mg and 410 mg per 100 g fresh weight of the beet.

The high pigment beet plants of the present invention was developed by crossing high pigment/high solid (HPHS) populations with high pigment/low solid (HPLS) populations and selecting for high pigment roots or by selecting within either the HPHS or HPLS populations. The beet root preferably has a pigment content of at least 310 mg per 100 g fresh weight of the beet root. Beet roots were selected for both increased pigment and high and low total dissolved solids. As levels of solids decrease, there is an increase in efficiency in preparing concentrated beet juice.

In the present invention a high pigment beet was produced by crossing a first high pigment beet population with another different beet or beet population. The high pigment beet population preferably has a pigment content of greater than 310 mg per 100 g fresh weight of the beet.

In another method of the present invention a high pigment beet was produced having a pigment content of at least 310 mg per 100 g fresh weight of the beet root. According to the method, a first high pigment beet is crossed with a second beet and the resultant beet seed is harvested. The high pigment beet used in the method has a pigment content of at least 310 mg per 100 g of fresh weight of the first beet. The pigment content of the beet produced by the method may also vary from 310 mg to over 400 mg per 100 g fresh weight of the beet root. A hybrid plant or its parts is produced by growing the high pigment beet. Seed is then produced from the hybrid plant.

EXAMPLES

The following examples are provided to further illustrate the present invention and are not intended to limit the invention beyond the limitations set forth in the appended claims.

Example 1

Development of Beet Population Cycle O

The effort to breed beets for higher concentrations of betalain pigment began with a first generation, designated Cycle 0, in 1981. The creation of the first generation is described in Watson & Gabelman, *J. Amer. Soc. Hort. Sci.* 109:386–391 (1984), and which is hereby incorporated by reference. In short, the method involved interpollination of plants in the heterogenous population followed by analysis and selection based on desirable horticultural characteristics. Families with the highest betalain concentrations were then chosen for future generational breeding.

The original beet population was formed from six open-pollinated cultivars chosen for high betalain pigment concentrations as described in Watson and Gabelman, (1984). Three of the selected cultivars were U.S. cultivars, namely, Garnet, Monoking Explorer, and Gladiator. The remaining three cultivars were European cultivars, namely, Regio, Rubia, and Boltardy. Twenty beet roots of each cultivar were selected and planted in a greenhouse. The roots were allowed to inter-pollinate. From each plant, equal quantities of seed were bulked and planted in Madison, Wis. The beets were then harvested and superior roots were selected. In particular, 150 roots were chosen for superior horticultural attributes, including shape, size, and total pigment concentration. These roots were planted in the greenhouse and randomly intermated. The seed from 105 of the plants were then harvested separately, producing 105 half-sib families.

The seeds were then planted to commence Cycle 0. More specifically, one hundred five half-sib families and four parental cultivars, namely, Reglo, Boltardy, Rubia, and Garnett, were planted in individual rows at the Walnut Street Garden in Madison, Wis. From these plants, ten roots from each row were selected based on the presence of desirable horticultural characteristics and harvested. The harvested roots were then analyzed for pigment and solids levels. Of these roots, twenty families having the highest red-violet betacyanins (BC) concentrations, were chosen. Plants in the original (initiation) population were chosen for high betalain concentration, but plants in the cyclical selection process were selected for BC. Within the selected families, seven roots with the highest pigment and solid concentrations (HPHS) and highest pigment and the lowest solids (HPLS) were chosen, resulting in 70 roots for seed production from each population. The pollination in red beet plants is open-pollinated, thus the pollen comes from the population at large. The seed harvested from each individual plant becomes a half-sib family, which is planted out in two replications in the field.

Samples of 50 grams were excised from individual roots or bulked samples were excised, consisting of 5 grams of each of ten roots per replicate from each family. The samples were frozen and then placed in a Waring™ blender with water and homogenized for five minutes at a high speed. The samples were then further homogenized with additional water in a polytron. Aliquots were taken from each sample in 15 milliliter amounts and centrifuged for 45 minutes at 15,000 rpm. One milliliter of supernatant from each sample was diluted to a total volume of 100 milliliters and spectrophotometric analyses were performed to determine total pigment. Total dissolved solids (TDS) were analyzed for a single drop of root exudate using a refractometer. Total pigment was represented at the combined level of betacyanin and betaxanthin (expressed in milligrams per 100 grams fresh weight).

Example 2

Population Cycles 1 through 4

For cycles 1 through 4, separate high dissolved solids and low dissolved solids populations were developed in parallel.

These populations were designated HPHS (high pigment high solids) and HPLS (high pigment low solids). The populations were planted in half sib families and the roots from the families were analyzed for betalain content. The details of the breeding of cycles 1 through 3 were described in Wolyn and Gabelman, *J. Amer. Hort. Sci.* 115(1):165–169 (1990), the disclosure of which is also hereby incorporated by reference.

Cycles one, two, three, and four were developed by planting HPHS and HPLS populations in two replicates of 70 half-sib families each. Twenty roots were selected from each family (10 from each of two replications) and analyzed for pigment and TDS. The seven roots with highest pigment and solids concentrations for HPHS and highest pigment and lowest solids for HPLS, were chosen within each of the ten best families producing 70 half-sib families for seed production.

Example 3

Population Cycles 5 through 7

Cycles five, six, and seven were developed following a similar selection procedure, except the HPLS population was selected for both high BC and low BX in addition to low TDS. Several other modifications were also made to the procedure during cycles five through seven. Only the top seven families were selected from the original ten. Also, only seven individuals were selected from each of the top seven families, resulting in a total of 49 individuals. Subsequently, three additional individuals were added to the selected population in HPLS and four individuals were added in the HPHS in an effort to restore the populations to a total of 70 individuals in the selected population in HPLS and 70 individuals in the selected population in HPHS.

Again, seven individuals were selected per top family. Thus, HPLS had 56 individuals (seven individuals from each of eight families) and HPHS had 42 individuals (seven individuals from each of six families). Selection was also done with a greater emphasis on TDS, trying to further separate HPHS and HPLS for TDS.

Example 4

Formation of Ruby Lake and Red Cloud Projects

Crossing of HPLS was then terminated and the HPHS continued with 42 individuals as the basis for the Ruby Lake Project. In this project, crosses were made between the highest families of HPLS and HPHS to begin Project Red Cloud.

A group of 60 high pigment individuals from this population were chosen for further advance, and became the Red Cloud population. Forty-two individuals were selected for Ruby Lake. The selection intensity for Red Cloud and Ruby Lake were set at ten individuals from the top six families.

Example 5

Population Cycles 10 and higher

In the tenth and eleventh cycles of the cross breeding, there were unexpected results. More specifically, the beets had pigment concentrations of at least 310 mg per 100 g fresh weight of the beet. In the tenth cycle, the Ruby Lake beets of the present invention had pigment contents of 313 mg per 100 g fresh weight. In the eleventh cycle, the Ruby Lake beets had 377 mg per 100 g fresh weight, and the Red Cloud beets had 350 mg per 100 g fresh weight. These unexpected levels of pigment of greater than 310 mg per 100 g fresh weight provide a beet that makes the preparation of red colorants both easier and less costly.

Example 6

Field Experiments and Pigment Measurements During the 1998 Field Season

Field experiments were conducted at the University of Wisconsin Horticulture Research Farm in Arlington, Wis. in 1998. This location has been the site of the beet breeding nursery for the past four years. Ro-neet and Pyramin were applied pre-plant and pre-emergent, respectively, to control weeds. Seed was sown in single row plots using Planet Jr. seeders with modified cone attachments during the second week of May, 1998. Plots were 3.7 m in length with a between-row spacing of 46 cm. Plots were harvested during the second week of August, 1998. Entries were planted in at least two. replications at the Arlington location using a randomized complete block design. For certain crosses, up to ten replicates were evaluated. For all Ruby Lake and Red Cloud samples, two replications were evaluated.

A randomly-chosen sample of 20 beets from each plot was removed from the harvest sample and placed in cold storage. For Ruby Lake and Red Cloud, samples of 50 g were excised by combining five grams of each of ten roots per replicate from each family. For other crosses, five grams of each of ten roots per replicate were also used for evaluation. Frozen samples were placed in a Waring blender with water and homogenized for five minutes at high speed. Samples were further homogenized with additional water in a polytron. Fifteen ml aliquots of each sample were centrifuged for 45 minutes at 15,000 rpm using a fixed angle rotor in a Sorvall RC5-B centrifuge. One ml of supernatant was diluted to a total volume of 100 ml and spectrophotometric analyses were performed to determine total pigment and BC:BX ratios. Total dissolved solids (TDS) were analyzed for a single drop of root exudate using a refractometer. BC and BX were calculated according to Wolyn and Gabelman (1990). Total pigment (TP) was represented as BC+BX. Data from bulked samples were used to calculate family means.

Example 7

The following Tables 1 through 5 are used to illustrate the level of pigment concentration in various genotypes. Table 1 shows results from trials grown in 1998 at Arlington, Wisconsin. In columns 2 and 3 of Table 1, betacyanin (BC) and betaxanthin (BX) concentrations are listed in mg per 100 gram fresh weight. The sum of betacyanin and betaxanthin (BC+BX) is shown in column 4, and the average total pigment concentration for selected families from the Ruby Lake population is listed in column 5.

TABLE 1

| | HPHS Population, C13 Ruby Lake 1998 | | | |
|---|---|---|---|---|
| Entry | Conc. BC | Conc. BX | BC + BX | Average |
| 3001 | 359.4 | 75.6 | 435.1 | |
| 3002 | 327.8 | 67.0 | 394.7 | |
| 3003 | 319.0 | 92.3 | 411.2 | |
| 3004 | 278.9 | 72.8 | 351.7 | |
| 3005 | 283.3 | 80.2 | 363.6 | |
| 3006 | 351.5 | 66.4 | 417.9 | |

TABLE 1-continued

HPHS Population, C13
Ruby Lake 1998

| Entry | Conc. BC | Conc. BX | BC + BX | Average |
|---|---|---|---|---|
| 3007 | 300.0 | 84.5 | 384.6 | |
| 3008 | 284.7 | 90.6 | 375.2 | |
| 3009 | 278.5 | 73.5 | 352.0 | 387.3 |
| 3010 | 216.9 | 74.2 | 291.1 | |
| 3011 | 281.6 | 86.8 | 368.4 | |
| 3012 | 262.7 | 77.3 | 340.0 | |
| 3013 | 251.7 | 80.0 | 331.6 | |
| 3014 | 273.7 | 90.8 | 364.5 | |
| 3015 | 227.5 | 64.5 | 292.0 | |
| 3016 | 230.5 | 69.4 | 300.0 | |
| 3017 | 271.9 | 77.6 | 349.5 | |
| 3018 | 270.1 | 63.9 | 334.0 | |
| 3019 | 220.0 | 80.9 | 300.9 | |
| 3020 | 245.9 | 76.6 | 322.5 | 326.8 |
| 3021 | 237.6 | 89.7 | 327.3 | |
| 3022 | 281.6 | 75.4 | 357.0 | |
| 3023 | 246.8 | 68.5 | 315.3 | |
| 3024 | 318.5 | 64.2 | 382.8 | |
| 3025 | 344.0 | 63.0 | 407.1 | |
| 3026 | 298.7 | 58.0 | 356.7 | |
| 3027 | 254.7 | 62.1 | 316.8 | |
| 3028 | 273.2 | 68.8 | 342.0 | |
| 3029 | 304.0 | 66.9 | 370.9 | |
| 3030 | 316.8 | 64.8 | 381.6 | |
| 3031 | 315.9 | 67.6 | 383.4 | 358.3 |
| 3032 | 242.9 | 76.5 | 319.3 | |
| 3033 | 327.3 | 77.9 | 405.3 | |
| 3034 | 278.5 | 68.1 | 346.6 | |
| 3035 | 307.1 | 87.5 | 394.5 | |
| 3036 | 300.0 | 69.5 | 369.6 | |
| 3037 | 242.4 | 77.8 | 320.2 | |
| 3038 | 310.2 | 81.6 | 391.7 | |
| 3039 | 200.2 | 67.5 | 267.7 | |
| 3040 | 312.4 | 68.2 | 380.6 | |
| 3041 | 299.2 | 80.6 | 379.8 | 357.5 |
| 3042 | 309.7 | 69.1 | 378.9 | |
| 3043 | 289.9 | 76.7 | 366.6 | |
| 3044 | 261.3 | 84.4 | 345.7 | |
| 3045 | 222.6 | 72.8 | 295.4 | |
| 3046 | 303.1 | 61.2 | 364.4 | |
| 3047 | 231.0 | 81.3 | 312.2 | |
| 3048 | 238.9 | 68.3 | 307.2 | |
| 3049 | 279.8 | 98.9 | 378.7 | |
| 3050 | 274.5 | 63.5 | 338.1 | |
| 3051 | 269.3 | 94.8 | 364.0 | |
| 3052 | 270.1 | 69.3 | 339.4 | 344.6 |
| 3053 | 295.2 | 103.0 | 398.2 | |
| 3054 | 275.9 | 60.1 | 335.9 | |
| 3055 | 237.1 | 82.1 | 319.2 | |
| 3056 | 256.9 | 61.9 | 318.9 | |
| 3057 | 275.0 | 92.8 | 367.7 | |
| 3058 | 263.5 | 82.4 | 345.9 | |
| 3059 | 314.6 | 70.4 | 385.0 | |
| 3060 | 272.8 | 70.7 | 343.5 | |
| 3061 | 244.6 | 83.1 | 327.7 | |
| 3062 | 237.1 | 78.5 | 315.6 | 345.8 |
| 3001 | 327.8 | 92.2 | 419.9 | |
| 3002 | 261.3 | 82.6 | 343.9 | |
| 3003 | 290.8 | 92.6 | 383.4 | |
| 3004 | 248.6 | 68.5 | 317.0 | |
| 3008 | 318.1 | 97.4 | 415.5 | 375.9 |
| 3010 | 284.2 | 108.7 | 392.9 | |
| 3012 | 258.3 | 81.3 | 339.5 | |
| 3014 | 267.1 | 83.0 | 350.0 | |
| 3016 | 266.6 | 93.9 | 360.5 | |
| 3020 | 247.3 | 98.3 | 345.6 | 357.7 |
| 3022 | 277.6 | 97.2 | 374.8 | |
| 3024 | 288.6 | 69.4 | 358.0 | |
| 3026 | 301.4 | 75.7 | 37.0 | |
| 3028 | 249.9 | 74.0 | 323.9 | |
| 3030 | 280.7 | 73.4 | 354.0 | |
| 3031 | 271.0 | 83.4 | 354.4 | 357.0 |
| 3032 | 248.6 | 97.3 | 345.8 | |
| 3033 | 287.3 | 80.6 | 367.9 | |

TABLE 1-continued

HPHS Population, C13
Ruby Lake 1998

| Entry | Conc. BC | Conc. BX | BC + BX | Average |
|---|---|---|---|---|
| 3034 | 236.7 | 64.8 | 301.5 | |
| 3035 | 289.1 | 71.6 | 360.7 | |
| 3037 | 242.9 | 94.5 | 337.3 | |
| 3040 | 255.2 | 81.7 | 336.9 | 341.7 |
| 3042 | 289.9 | 85.1 | 375.0 | |
| 3043 | 278.9 | 75.8 | 354.7 | |
| 3046 | 293.4 | 59.9 | 353.3 | |
| 3049 | 266.2 | 82.1 | 348.2 | |
| 3050 | 272.3 | 79.3 | 351.6 | |
| 3052 | 280.7 | 53.6 | 334.2 | 352.9 |
| 3053 | 272.8 | 74.9 | 347.7 | |
| 3055 | 260.9 | 68.3 | 329.2 | |
| 3056 | 267.1 | 65.6 | 332.6 | |
| 3058 | 278.1 | 62.9 | 340.9 | |
| 3059 | 279.8 | 73.1 | 352.9 | |
| 3060 | 269.7 | 62.8 | 332.5 | |
| 3061 | 232.7 | 75.2 | 308.0 | |
| 3062 | 282.0 | 73.5 | 355.5 | 337.4 |
| St. Dev. | 32.0 | Average | 352.3 | |

Example 8

Table 2 shows results from trials grown in 1998 at Arlington, Wis. Columns 2 and 3 in Table 2 show betacyanin (BC) and betaxanthin (BX) concentrations in mg per 100 gram fresh weight. The sum of betacyanin and betaxanthin (BC+BX) is listed in column 4, and the average total pigment concentration for selected families from the Red Cloud population is shown in column 5.

TABLE 2

HPHS x HPLS
Red Cloud 1998 - Rep. 1

| Entry | Conc. BC | Conc. BX | BC + BX | Average |
|---|---|---|---|---|
| 2001 | 272.8 | 80.9 | 353.7 | |
| 2002 | 267.9 | 89.2 | 357.2 | |
| 2003 | 289.9 | 90.5 | 380.4 | |
| 2004 | 260.0 | 95.6 | 355.6 | |
| 2005 | 270.6 | 78.7 | 349.3 | |
| 2006 | 231.0 | 75.3 | 306.2 | |
| 2007 | 282.9 | 93.6 | 376.5 | |
| 2008 | 264.0 | 89.4 | 353.4 | |
| 2009 | 228.3 | 79.2 | 307.5 | 348.9 |
| 2010 | 246.8 | 87.7 | 334.5 | |
| 2011 | 320.7 | 91.7 | 412.4 | |
| 2012 | 260.5 | 82.9 | 343.3 | |
| 2013 | 246.8 | 99.7 | 346.5 | |
| 2014 | 213.4 | 73.7 | 287.0 | |
| 2015 | 242.0 | 82.2 | 324.2 | |
| 2016 | 267.5 | 70.8 | 338.3 | |
| 2017 | 284.2 | 60.1 | 344.3 | |
| 2018 | 277.6 | 90.0 | 367.6 | 344.2 |
| 2019 | 237.6 | 58.5 | 296.1 | |
| 2020 | 275.4 | 80.0 | 356.4 | |
| 2021 | 314.1 | 88.6 | 402.7 | |
| 2022 | 231.0 | 74.7 | 305.6 | |
| 2023 | 3233.8 | 94.8 | 418.6 | |
| 2024 | 383.6 | 18.5 | 402.1 | |
| 2025 | 293.0 | 69.6 | 362.6 | |
| 2026 | 260.0 | 67.4 | 327.4 | |
| 2027 | 285.1 | 74.2 | 359.3 | |
| 2028 | 317.6 | 88.5 | 406.2 | |
| 2029 | 318.1 | 87.2 | 405.3 | 358.9 |
| 2030 | 248.6 | 82.9 | 331.4 | |
| 2031 | 296.5 | 80.4 | 376.9 | 379.9 |
| 2032 | 307.5 | 76.5 | 384.0 | |

TABLE 2-continued

HPHS x HPLS
Red Cloud 1998 - Rep. 1

| Entry | Conc. BC | Conc. BX | BC + BX | Average |
|---|---|---|---|---|
| 2033 | 299.2 | 75.8 | 375.0 | |
| 2034 | 259.1 | 88.7 | 347.9 | |
| 2035 | 278.1 | 98.9 | 376.9 | |
| 2036 | 284.2 | 69.1 | 353.3 | |
| 2037 | 268.4 | 78.3 | 346.7 | |
| 2038 | 344.9 | 75.3 | 420.3 | |
| 2039 | 278.9 | 78.2 | 357.1 | |
| 2040 | 217.8 | 90.7 | 308.5 | 363.3 |
| 2041 | 282.5 | 79.9 | 362.4 | |
| 2042 | 282.0 | 95.1 | 377.1 | |
| 2043 | 301.4 | 100.9 | 402.2 | 380.6 |
| 2044 | 278.9 | 96.2 | 375.1 | |
| 2045 | 267.1 | 87.8 | 354.8 | |
| 2046 | 295.6 | 66.9 | 362.5 | |
| 2047 | 311.5 | 100.9 | 412.4 | |
| 2048 | 321.2 | 98.1 | 419.3 | |
| 2049 | 310.2 | 111.0 | 421.1 | |
| 2050 | 288.6 | 82.0 | 370.6 | 388.0 |
| REP 2 | | | | |
| 2001 | 249.0 | 76.1 | 325.1 | |
| 2004 | 326.0 | 78.4 | 404.4 | |
| 2005 | 245.9 | 72.4 | 318.3 | |
| 2006 | 243.3 | 63.1 | 306.4 | |
| 2008 | 283.3 | 85.6 | 369.0 | |
| 2009 | 223.9 | 95.7 | 319.7 | 340.5 |
| 2010 | 236.3 | 69.8 | 306.1 | |
| 2011 | 251.7 | 79.4 | 331.0 | |
| 2012 | 214.7 | 85.2 | 299.9 | |
| 2013 | 209.9 | 84.5 | 294.4 | |
| 2014 | 231.0 | 87.3 | 318.2 | |
| 2016 | 274.1 | 68.5 | 342.6 | |
| 2017 | 256.1 | 89.2 | 345.3 | |
| 2018 | 308.4 | 99.6 | 408.0 | 330.7 |
| 2019 | 180.4 | 70.3 | 250.7 | |
| 2020 | 256.1 | 86.8 | 342.9 | |
| 2021 | 279.4 | 83.4 | 362.8 | |
| 2022 | 214.3 | 84.1 | 298.4 | |
| 2023 | 244.2 | 86.2 | 330.4 | |
| 2024 | 225.3 | 81.5 | 306.7 | |
| 2025 | 264.0 | 75.0 | 339.0 | |
| 2027 | 234.1 | 84.4 | 318.4 | 318.7 |
| 2028 | 231.9 | 83.3 | 315.2 | |
| 2029 | 274.1 | 93.1 | 367.2 | |
| 2030 | 238.9 | 77.9 | 316.8 | |
| 2031 | 271.9 | 78.8 | 350.7 | 337.5 |
| 2032 | 304.4 | 101.0 | 405.4 | |
| 2033 | 261.8 | 83.0 | 344.8 | |
| 2034 | 255.2 | 99.1 | 354.3 | |
| 2035 | 240.2 | 87.6 | 327.8 | |
| 2036 | 229.7 | 85.9 | 315.6 | |
| 2037 | 274.5 | 110.9 | 385.5 | |
| 2038 | 319.8 | 96.8 | 416.6 | |
| 2039 | 252.1 | 88.8 | 340.9 | |
| 2040 | 225.7 | 80.1 | 305.8 | 355.2 |
| 2043 | 299.6 | 97.9 | 397.5 | 397.5 |
| 2044 | 237.6 | 92.7 | 330.3 | |
| 2045 | 229.2 | 74.1 | 303.3 | |
| 2046 | 270.1 | 74.7 | 344.8 | |
| 2047 | 265.7 | 79.8 | 345.6 | |
| 2048 | 264.4 | 86.9 | 351.3 | |
| 2049 | 303.6 | 101.3 | 404.9 | |
| 2050 | 260.9 | 92.9 | 353.8 | 347.7 |
| | | Average | 351.9 | |
| | | St. Dev. | 36.8 | |

Example 9

Table 3 shows results from field trials grown in 1997 at Arlington, Wis. Columns 2 and 3 of Table 3 show betacyanin (BC) and betaxanthin (BX) concentrations in mg per 100 gram fresh weight. The sum of betacyanin and betaxanthin (BC+BX) is listed in column 4.

TABLE 3

Ruby Lake 1997 Rep 2

| Entry | Conc. BC | Conc. BX | BC + BX |
|---|---|---|---|
| 3001 | 305.3 | 105.5 | 410.8 |
| 3002 | 311.9 | 109.8 | 421.7 |
| 3003 | 281.1 | 117.0 | 398.1 |
| 3004 | 292.1 | 97.5 | 389.7 |
| 3005 | 263.1 | 94.5 | 357.6 |
| 3006 | 288.6 | 128.2 | 416.8 |
| 3007 | 359.9 | 136.7 | 496.5 |
| 3008 | 240.7 | 116.9 | 357.5 |
| 3009 | 243.7 | 117.6 | 361.3 |
| 3010 | 282.5 | 117.1 | 399.6 |
| 3011 | 267.1 | 117.8 | 384.8 |
| 3012 | 272.8 | 106.1 | 378.9 |
| 3013 | 294.8 | 114.6 | 409.4 |
| 3014 | 244.6 | 107.7 | 352.3 |
| 3015 | 285.1 | 124.6 | 409.7 |
| 3016 | 242.0 | 106.2 | 348.2 |
| 3017 | 284.7 | 139.2 | 423.8 |
| 3018 | 298.7 | 121.0 | 419.7 |
| 3019 | 217.8 | 115.3 | 333.1 |
| 3020 | 253.9 | 96.6 | 350.5 |
| 3021 | 275.0 | 96.4 | 371.3 |
| 3022 | 267.1 | 97.4 | 364.4 |
| 3023 | 231.0 | 92.1 | 323.0 |
| 3024 | 267.5 | 93.6 | 361.1 |
| 3025 | 298.7 | 112.0 | 410.7 |
| 3026 | 220.0 | 83.9 | 303.9 |
| 3027 | 294.8 | 104.4 | 399.2 |
| 3028 | 263.1 | 106.5 | 369.6 |
| 3029 | 268.4 | 99.9 | 368.3 |
| 3030 | 276.3 | 122.3 | 398.6 |
| 3031 | 315.0 | 126.1 | 441.1 |
| 3032 | 236.3 | 114.2 | 350.5 |
| 3033 | 212.5 | 98.6 | 311.1 |
| 3034 | 267.9 | 106.0 | 374.0 |
| 3035 | 273.7 | 121.4 | 395.1 |
| 3036 | 231.4 | 120.7 | 352.1 |
| 3037 | 319.8 | 132.8 | 452.6 |
| 3038 | 259.1 | 96.5 | 355.7 |
| 3039 | 293.9 | 83.1 | 377.0 |
| 3040 | 284.7 | 104.4 | 389.0 |
| 3041 | 273.7 | 96.2 | 369.9 |
| 3042 | 299.2 | 113.6 | 412.8 |
| 3043 | 264.9 | 110.7 | 375.6 |
| 3044 | 271.5 | 112.0 | 383.5 |
| 3045 | 278.5 | 110.7 | 389.2 |
| 3046 | 262.7 | 111.5 | 374.2 |
| 3047 | 264.4 | 99.5 | 363.9 |
| 3048 | 242.4 | 97.0 | 339.4 |
| 3049 | 241.1 | 91.5 | 332.6 |
| 3050 | 260.5 | 111.7 | 372.1 |
| 3051 | 274.1 | 102.1 | 376.2 |
| 3052 | 244.2 | 81.4 | 325.6 |
| 3053 | 224.4 | 111.2 | 335.6 |
| 3054 | 269.3 | 107.4 | 376.6 |
| 3055 | 306.6 | 97.8 | 404.5 |
| 3056 | 259.1 | 91.7 | 350.9 |
| | | Average | 376.6 |
| REP 2 | | | |
| 3001 | 266.2 | 110.9 | 377.0 |
| 3002 | 238.0 | 107.6 | 345.6 |
| 3003 | 263.1 | 128.7 | 391.8 |
| 3004 | 310.2 | 109.2 | 419.3 |
| 3005 | 264.0 | 94.8 | 358.8 |
| 3006 | 265.7 | 102.6 | 368.4 |
| 3007 | 356.8 | 127.5 | 484.4 |
| 3008 | 266.6 | 118.5 | 385.1 |
| 3009 | 250.3 | 120.0 | 370.4 |
| 3010 | 275.0 | 127.0 | 401.9 |
| 3011 | 287.7 | 95.5 | 383.2 |
| 3012 | 250.3 | 100.8 | 351.2 |
| 3013 | 301.4 | 111.1 | 412.4 |
| 3015 | 290.8 | 110.6 | 401.4 |
| 3017 | 248.1 | 113.6 | 361.8 |
| 3018 | 277.6 | 116.4 | 394.0 |
| 3019 | 246.8 | 117.7 | 364.5 |

TABLE 3-continued

Ruby Lake 1997 Rep 2

| Entry | Conc. BC | Conc. BX | BC + BX |
|---|---|---|---|
| 3020 | 267.5 | 102.6 | 370.1 |
| 3021 | 295.2 | 96.4 | 391.6 |
| 3022 | 262.7 | 104.3 | 367.0 |
| 3023 | 247.3 | 101.9 | 349.2 |
| 3024 | 292.1 | 104.1 | 396.3 |
| 3025 | 299.6 | 100.9 | 400.5 |
| 3026 | 228.3 | 87.0 | 315.3 |
| 3027 | 299.6 | 96.7 | 396.3 |
| 3028 | 308.0 | 90.1 | 398.1 |
| 3029 | 266.2 | 117.5 | 383.6 |
| 3030 | 325.1 | 103.3 | 428.4 |
| 3031 | 290.4 | 117.9 | 408.3 |
| 3032 | 279.4 | 131.4 | 410.8 |
| 3033 | 254.3 | 109.0 | 363.3 |
| 3034 | 246.4 | 137.6 | 384.0 |
| 3035 | 276.7 | 119.1 | 395.9 |
| 3036 | 246.4 | 110.6 | 357.0 |
| 3037 | 276.3 | 120.5 | 396.8 |
| 3038 | 229.7 | 78.7 | 308.4 |
| 3039 | 287.3 | 69.2 | 356.5 |
| 3040 | 319.4 | 91.5 | 410.9 |
| 3041 | 283.3 | 112.0 | 395.4 |
| 3042 | 278.5 | 116.7 | 395.2 |
| 3043 | 228.3 | 93.6 | 321.9 |
| 3044 | 279.8 | 106.7 | 386.5 |
| 3045 | 311.5 | 126.7 | 438.2 |
| 3046 | 277.2 | 94.4 | 371.6 |
| 3047 | 303.1 | 117.6 | 420.8 |
| 3048 | 233.6 | 105.5 | 339.1 |
| 3049 | 235.8 | 104.2 | 340.0 |
| 3050 | 247.7 | 102.4 | 350.1 |
| 3051 | 271.0 | 87.6 | 358.6 |
| 3052 | 289.5 | 95.5 | 384.9 |
| 3053 | 256.9 | 103.9 | 360.9 |
| 3054 | 273.2 | 97.6 | 370.8 |
| 3055 | 267.1 | 81.8 | 348.8 |
| 3056 | 220.4 | 100.6 | 321.0 |
|  |  | Average | 378.9 |

Example 10

Table 4 shows the results of field trials grown in 1997 at Arlington, Wis. Columns 3 and 4 of Table 4 show concentrations in mg per 100 gram fresh weight of the sum of betacyanin and betaxanthin (BC+BX) for selected families from the Red Cloud population.

TABLE 4

Red Cloud 1997

| Entry | Pedigree | Rep. 1 BC + BX | Rep. 2 BC + BX |
|---|---|---|---|
| 2001 | (HPLSmHPHS) #2 | 335.9 | 392.9 |
| 2002 | (HPLSmHPHS) #2 | 334.2 | 265.0 |
| 2003 | (HPLSmHPHS) #2 | 325.6 | 293.1 |
| 2004 | (HPLSmHPHS) #2 | 331.0 | 358.1 |
| 2005 | (HPLSmHPHS) #3 | 355.5 | 353.8 |
| 2006 | (HPLSmHPHS) #3 | 343.8 | 293.3 |
| 2007 | (HPLSmHPHS) #3 | 347.6 | 309.7 |
| 2008 | (HPLSmHPHS) #3 | 362.1 | 354.0 |
| 2009 | (HPLSmHPHS) #3 | 328.1 | 279.3 |
| 2010 | (HPLSmHPHS) #4 | 402.0 | 381.1 |
| 2011 | (HPLSmHPHS) #4 | 376.7 | 348.2 |
| 2012 | (HPLSmHPHS) #4 | 367.7 | 359.1 |
| 2013 | (HPLSmHPHS) #4 | 373.1 | 389.6 |
| 2014 | (HPLSmHPHS) #4 | 337.8 | 349.6 |
| 2015 | (HPLSmHPHS) #4 | 316.1 | 301.6 |
| 2016 | (HPLSmHPHS) #4 | 351.3 | 338.3 |
| 2017 | (HPLSmHPHS) #4 | 366.8 | 387.5 |
| 2018 | (HPLSmHPHS) #4 | 376.2 | 343.2 |
| 2019 | (HPLSmHPHS) #4 | 335.9 | 306.0 |
| 2020 | (HPLSmHPHS) #5 | 357.7 | 360.2 |
| 2021 | (HPLSmHPHS) #5 | 320.2 | 329.0 |
| 2022 | (HPLSmHPHS) #5 | 368.5 | 371.9 |
| 2023 | (HPLSmHPHS) #5 | 399.2 | 365.3 |
| 2024 | (HPLSmHPHS) #5 | 401.4 | 412.3 |
| 2025 | (HPLSmHPHS) #6 | 393.4 | 453.0 |
| 2026 | (HPLSmHPHS) #6 | 391.6 | 309.5 |
| 2027 | (HPLSmHPHS) #6 | 362.9 | 344.6 |
| 2028 | (HPLSmHPHS) #6 | 372.0 | 350.4 |
| 2029 | (HPLSmHPHS) #6 | 375.1 | 346.2 |
| 2030 | (HPLSmHPHS) #6 | 388.7 | 374.6 |
| 2031 | (HPLSmHPHS) #6 | 306.2 | 314.8 |
| 2032 | (HPLSmHPHS) #6 | 323.9 | 281.9 |
| 2033 | (HPLSmHPHS) #6 | 392.8 | 398.7 |
| 2034 | (HPLSmHPHS) #7 | 362.0 | 349.9 |
| 2035 | (HPLSmHPHS) #7 | 390.6 | 356.0 |
| 2036 | (HPLSmHPHS) #7 | 278.9 | 352.3 |
| 2037 | (HPLSmHPHS) #7 | 353.8 | 334.1 |
| 2038 | (HPLSmHPHS) #7 | 353.9 | 341.4 |
| 2039 | (HPLSmHPHS) #8 | 339.9 | 386.6 |
| 2040 | (HPLSmHPHS) #8 | 296.9 | 309.4 |
| 2041 | (HPLSmHPHS) #8 | 333.0 | 319.8 |
| 2042 | (HPLSmHPHS) #8 | 408.5 | 376.5 |
| 2043 | (HPLSmHPHS) #9 | 326.3 | 334.9 |
| 2044 | (HPLSmHPHS) #9 | 340.7 | 332.5 |
| 2045 | (HPLSmHPHS) #9 | 334.1 | 383.6 |
| 2046 | (HPLSmHPHS) #9 | 325.4 | 358.8 |
| 2047 | (HPLSmHPHS) #9 | 347.9 | 350.8 |
| 2048 | (HPLSmHPHS) #9 | 309.4 | 367.0 |
| 2049 | (HPLSmHPHS) #9 | 402.6 | 372.1 |
| 2050 | (HPLSmHPHS) #9 | 369.9 | 267.2 |
| 2051 | (HPLSmHPHS) #9 | 399.6 | 375.3 |
| 2052 | (HPLSmHPHS) #9 | 354.8 | 307.4 |
| 2053 | (HPLSmHPHS) #10 | 371.9 | 328.2 |
| 2054 | (HPLSmHPHS) #10 | 302.2 | 319.1 |
| 2055 | (HPLSmHPHS) #10 | 394.2 | 366.1 |
|  | Average | 354.9 | 345.5 |
|  | Total Average | 350.2 |  |

Deposit Information

A representative sample of the high pigment red beet population HPHS has been placed on deposit with the American Type Culture Collection (ATCC), Manassas, Va., under Deposit Accession Number PTA-856 on Oct. 18, 1999.

A representative sample of the high pigment red beet population HPLS has been placed on deposit with the American Type Culture Collection (ATCC), Manassas, Virginia, under Deposit Accession Number PTA-857 on Oct. 18, 1999.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A beet plant having a pigment concentration of at least 310 mg per 100 g fresh weight of the root.

2. A beet seed produced from the beet plant of claim 1.

3. The beet plant of claim 1 wherein the pigment concentration is between 310 mg and 330 mg per 100 g fresh weight of the root.

4. The beet plant of claim 1 wherein the pigment concentration is between 330 mg and 350 mg per 100 g fresh weight of the root.

5. The beet plant of claim 1 wherein the pigment concentration is between 350 mg and 370 mg per 100 g fresh weight of the root.

6. The beet plant of claim 1 wherein the pigment concentration is between 370 mg and 390 mg per 100 g fresh weight of the root.

7. The beet plant of claim 1 wherein the pigment concentration is between 390 mg and 410 mg per 100 g fresh weight of the root.

8. The beet plant of claim 1 wherein the pigment concentration is greater than 410 mg per 100 g fresh weight of the root.

9. Pollen of the plant of claim 1.

10. An ovule of the plant of claim 1.

11. A method of producing a high pigment beet by:
   a) crossing an HPHS beet population with an HPLS beet population;
   b) harvesting seed from said cross;
   c) growing said seed to produce beet plants and roots; and
   d) selecting beet plants having a pigment content of at least 310 mg per 100 g fresh weight of the root.

12. The method of claim 11 wherein the pigment concentration is between 310 mg and 330 mg per 100 g fresh weight of the root.

13. The method of claim 11 wherein the pigment concentration is between 330 mg and 350 mg per 100 g fresh weight of the root.

14. The method of claim 11 wherein the pigment concentration is between 350 mg and 370 mg per 100 g fresh weight of the root.

15. The method of claim 11 wherein the pigment concentration is between 370 mg and 390 mg per 100 g fresh weight of the root.

16. The method of claim 11 wherein the pigment concentration is between 390 mg and 410 mg per 100 g fresh weight of the root.

17. The method of claim 11 wherein the pigment concentration is greater than 410 mg per 100 g fresh weight of the root.

18. A method for producing a high pigment beet, comprising crossing a first beet plant with a second beet plant having a pigment concentration of greater than 310 per 100 g fresh weight of the root; and harvesting the resultant $F_1$ hybrid beet.

19. The method of claim 18 wherein the pigment concentration of said second beet is between 310 mg and 330 mg per 100 g fresh weight of the root.

20. The method of claim 18 wherein the pigment concentration of said second beet is between 330 mg and 350 mg per 100 g fresh weight of the root.

21. The method of claim 18 wherein the pigment concentration of said second beet is between 350 mg and 370 mg per 100 g fresh weight of the root.

22. The method of claim 18 wherein the pigment concentration of said second beet is between 370 mg and 390 mg per 100 g fresh weight of the root.

23. The method of claim 18 wherein the pigment concentration of said second beet is between 390 mg and 410 mg per 100 g fresh weight of the root.

24. The method of claim 18 wherein the pigment concentration of said second beet is greater than 410 mg per 100 g fresh weight of the root.

25. Viable beet roots to which the increased pigment characteristic is transferred from seeds deposited under ATCC Accession No. PTA-956 in succeeding generations.

26. Viable beet roots to which the increased pigment characteristic is transferred from seeds deposited under ATCC Accession No. PTA-857 in succeeding generations.

27. Beet seeds and plants to which the increased pigment characteristic is transferred from ATCC Accession number PTA-856 in succeeding generations.

28. Beet seeds and plants to which the increased pigment characteristic is transferred from ATCC Accession number PTA-857 in succeeding generations.

* * * * *